(12) United States Patent
Gatto (10) Patent No.: US 10,300,012 B2
(45) Date of Patent: May 28, 2019

(54) TOPICAL COMPOSITION COMPRISING EXTRACTS OF BOLDO AND OF MEADOWSWEET, INTENDED FOR AN ANIMAL, AND USES THEREOF

(71) Applicant: VIRBAC SA, Carros (FR)

(72) Inventor: Hugues Gatto, Saint Paul de Vence (FR)

(73) Assignee: VIRBAC, Carros (FR)

( * ) Notice: Subject to any disclaimer, the term of this patent is extended or adjusted under 35 U.S.C. 154(b) by 38 days.

(21) Appl. No.: 15/109,363

(22) PCT Filed: Nov. 20, 2014

(86) PCT No.: PCT/FR2014/000249
§ 371 (c)(1),
(2) Date: Jun. 30, 2016

(87) PCT Pub. No.: WO2015/101722
PCT Pub. Date: Jul. 9, 2015

(65) Prior Publication Data
US 2016/0324769 A1    Nov. 10, 2016

(30) Foreign Application Priority Data
Dec. 31, 2013   (FR) .................................... 13 03124

(51) Int. Cl.
| | | |
|---|---|---|
| *A61K 36/00* | (2006.01) | |
| *A61K 9/00* | (2006.01) | |
| *A61K 36/185* | (2006.01) | |
| *A61K 36/73* | (2006.01) | |

(52) U.S. Cl.
CPC .......... *A61K 9/0017* (2013.01); *A61K 36/185* (2013.01); *A61K 36/73* (2013.01)

(58) Field of Classification Search
CPC ...................................................... A61K 36/00
See application file for complete search history.

(56) References Cited

U.S. PATENT DOCUMENTS

| | | | |
|---|---|---|---|
| 2004/0091493 A1 | 5/2004 | Perrier et al. | |
| 2010/0303854 A1* | 12/2010 | Hines ........................ | A61K 8/97 424/195.17 |

FOREIGN PATENT DOCUMENTS

| | | | |
|---|---|---|---|
| EP | 2 322 138 A2 | 5/2011 | |
| FR | 2 843 125 A1 | 2/2004 | |
| FR | 2 863 893 A1 | 6/2005 | |
| FR | 2 897 778 A1 | 8/2007 | |
| FR | 2916634 A1 * | 12/2008 | ............... A61K 8/60 |
| JP | 2000-336024 A | 12/2000 | |

OTHER PUBLICATIONS

Banovic et al., "In vitro comparison of the effectiveness of polihexanide and chlorhexidine against canine isolates of *Staphylococcus pseudintermedius*, Pseudomonas aeruginosa and Malassezia pachydermatis", Veterinary Dermatology, vol. 24, No. 4, Jun. 21, 2013, pp. 409-e89; in English; cited in the ISR (7 pages).
Yildirim et al., "Biological activities of meadowsweet (*Filipendula ulmaria* (L.) *maxim*)", Planta Medica, vol. 75, No. 9, Jul. 1, 2009, p. 1066; XP009179137; in English; cited in the ISR.
Vila et al., "Composition and Antimicrobial Activity of the Essential Oil of Peumus boldus Leaves", Planta Medica, vol. 55, No. 2, Mar. 1999, pp. 178-179, XP-002727355; in English; cited in the ISR.
(HMPC) Committee on Herbal Medicinal Products, "Assessment Report on Peumus Boldus Molina, Folium", EMEA European Medicines Agency, Jan. 14, 2009, pp. 1-15; in English; cited in the ISR.
(HMPC) Committee on Herbal Medicinal Products, "Assessment report on *Filipendula ulmaria* (L.) Maxim., *herba* and *Filipendula ulmaria* (L.) Maxim., *flos*", EMEA European Medicines Agency, Jan. 12, 2011, pp. 1-18; in English; cited in the ISR.
International Search Report and Written Opinion dated Apr. 7, 2015 issued in corresponding application No. PCT/FR2014/000249; w/ English translation (18 pages).
Japanese Office Action dated Jul. 10, 2018 in counterpart application No. JP 2016-561085 (with English machine translation; 6 pages) (D1, EP2322138; D3, Yildirim et al., D4, Vila et al., and D6, Banovic et al. cited in the Japanese Office Action are not isted in this IDS since they were already listed in the IDS filed Jun. 30, 2016).
Bojar et al., "Review: the human cutaneous microflora and factors controlling colonisation", World Journal of Microbiology & Biotechnology, vol. 18, pp. 889-903 (2002) (in English; D5 cited in the Japanese Office Action dated Jul. 10, 2018).

* cited by examiner

*Primary Examiner* — Qiuwen Mi
(74) *Attorney, Agent, or Firm* — Westerman, Hattori, Daniels & Adrian, LLP (57) ABSTRACT

The invention relates to a topical veterinary composition for animals. It is characterized in that it comprises, in a physiologically acceptable medium, extracts of boldo *Peumus boldus* and extracts of meadowsweet *Spiraea ulmaria*. The invention applies in particular to preventing or treating or to assisting with the control of microbial infections.

21 Claims, 4 Drawing Sheets

TOPICAL COMPOSITION COMPRISING EXTRACTS OF BOLDO AND OF MEADOWSWEET, INTENDED FOR AN ANIMAL, AND USES THEREOF

This invention relates to a composition for topical administration intended for an animal, comprising extracts of plants stimulating the cellular synthesis of antimicrobial peptides, in particular for its use in preventing, treating or assisting with the control of microbial infections. More particularly, the invention relates to a composition for topical administration intended for a domestic animal comprising extracts of boldo, *Peumus boldus*, and extracts of meadowsweet *Spiraea ulmaria*.

BACKGROUND ART

The main function of the skin consists in providing protection between the hostile earthly world and the interior of the organism. This defensive function is made possible by the two following main functions:

(i) an epidermal barrier function. It is located on the exterior portion (stratum corneum) of the most superficial layer of the skin (the epidermis). The structure of the corneous layer can be compared to a wall of bricks, wherein the bricks represent the dead cells (cornocytes) and the mortar, an intercellular matrix organized into a lipid lamellar structure. This barrier protects the organism from chemical, microbiological and physical aggressions and regulates the exchanges in water between the organism and the environment;

(ii) the cutaneous immune system (CIS). The CIS is able to induce an inflammatory response against exterior aggressions. The CIS can be divided into 2 portions, an innate portion and an adaptive portion:

The innate immune system corresponds to the first-line mechanism, which is non-specific against the microbial invasion. In the case where the physical barrier is broken, the innate immune response is activated in order to eliminate the aggressors. The innate system uses pre-existing receptors which can bind to molecules and/or molecular patterns commonly found on many microbes. However, this innate immune system remains unable to develop a memory of aggressions and therefore effective protection with regards to reinfection;

The adaptive immune system consists of a delayed and specific immune response. It is capable of recognizing more specifically exterior and antigen aggressions, destroying them and retaining in memory the aggressions incurred.

Keratinocytes are cells that constitute 90% of the epidermis and appendages, i.e. the nails, hair, fur, feathers, and scales. They play an important role in the local immune function. They indeed produce interleukins and cytokines aiming to preserve the homeostasis i.e. the balance of the barrier.

The antimicrobial peptides (AMPs) of the innate immune system, such as cathelicidins or beta-defensins, which are produced by the skin, are stored in lamellar bodies and are then delivered to the corneous layer.

These antimicrobial peptides AMPs are small peptides having between about 12 and 50 amino acids. They are considered as one of the key elements of the innate immune system, servant for the defense of multicellular organisms during microbial infections. They have properties of direct inhibition against microbial pathogens. They attach and fit into the microbial phospholipid bilayer, inducing a inducing a rupture of the microbial membrane then a lysis.

There are a large number of AMPs. The main known AMPs are beta-defensins (BD) and cathelicidins (Cath). Beta-defensins and cathelicidins have been identified in the skin (epidermis) of a large number of mammals, in particular humans, the dog, the cat and the horse. These AMPs are synthesized by leukocytes and epithelial mucosal tissue. However, they are mainly produced by keratinocytes. They are expressed or induced by bacterial components (lipopolysaccharides) or by pro-inflammatory mediators (by way of example: IL-6 for Interleukin-6, IL-8, interferon-gamma, TNF-alpha).

The beta-defensins (BD) have antimicrobial activity and play an immunomodulatory role (by chemotactic activity). In animals and in particular in dogs, existing data on the expression of beta-defensins and in particular cBD103 is contradictory. As such, the mRNA expression of cBD103 in atopic dogs would be lower than the mRNA expression of cBD103 in healthy dogs according to studies presented by Van Damme et al., Mol Immuno 2009. This mRNA expression between atopic dogs and healthy dogs would be similar according to studies presented by Leonard et al., J Innate Immunol 2012. Finally, according to the studies of Santoro et al., Vet Derm 2013 the mRNA expression of cBD103 in atopic dogs would be increased with respect to healthy dogs.

Likewise, according to Santoro et al., Vet Derm 2013, the mRNA expression of cBD103 in skin lesions (lesional sites) would be increased with respect to non-lesional sites. On the other hand, according to studies presented by Leonard et al., J Innate Immunol 2012, the mRNA expression of cBD103 would substantially similar between lesional and non-lesional sites.

The cathelicidins (Cath) are also powerful antimicrobial agents. They have an intrinsic ability to kill Gram-negative and Gram-positive bacteria, fungi and viruses. They also promote a host response by triggering the recruitment of immunocompetent cells and release of cytokines.

It has been shown that an alteration of the expression of AMPs in subjects with an alteration of the skin barrier (for example during skin lesions or during dermatitis, such as canine or feline atopic dermatitis, *Malassezia* dermatitus, during pyoderma, chronic ear infections, or fungal or bacterial infections) may predispose the host to secondary infections. The expression levels of beta-defensins and cathelicidin of atopic dogs are modified relative to their expression levels in healthy dogs.

The alterations of the skin barrier can be induced by the pathology in a primary manner or secondarily by pruritus. Atopic dermatitis in particular is a chronic pruritic skin disease that appears in numerous species. Animals with atopic dermatitis have a genetic predisposition to develop allergic reactions with respect to environmental antigens, such as pollen or mold. This results in excessive production of reaginic antibodies (IgE). An estimated 10% of dogs suffer from atopy. Skin lesions generated by this disease are greatly aggravated by licking, scratching, and bacterial infections. Atopic dogs furthermore exhibit high rates of *Staphylococcus pseudintermedius* and *Malassezia pachydermatis*.

SUMMARY OF THE INVENTION

Given the foregoing, there exists therefore a need to develop a composition for topical administration intended for an animal that is capable of stimulating the innate immunity of the skin, by increasing the expression of the beta-defensins and/or of the cathelicidins, more preferably in dogs or in cats.

It was shown that among 300 substances, the extract of boldo is the most effective substance for stimulating the expression of human beta-defensin hBD-3. In addition to its specific action on hBD-3, the extract of boldo, consisting in particular of an alcaloid, boldine, has a wide spectrum of action against Gram-positive and Gram-negative bacteria. Boldo extract is also known to be effective against *Staphylococcus aureus*.

Formulated at 4%, the extract of boldo makes it possible in particular to reduce skin imperfections in subjects with severe skin disorders.

Application FR2843125 discloses pharmaceutical compositions comprising an active ingredient capable of stimulating the human expression of hBD-2 and/or hBD-3. Among the active ingredients that can be used, mention can be made of the extract of boldo.

Application FR2863893 describes in turn the use of an active ingredient capable of stimulating the human expression of hBD-2 and/or hBD-3 for the manufacture of a cosmetic composition intended to exert bactericidal and/or fungicidal activity on the skin. Among the active ingredients that can be used, mention can also be made of the extract of boldo.

The Betapur™ product marketed by the company BASF comprises the extract of boldo, *Peumus boldus*, and induces the production of beta-defensins without causing inflammation in human keratinocytes.

In humans, it has also been shown that the Dermapur® product marketed by the company Silab made it possible to preserve the ecosystem of the skin by stimulating the cellular synthesis of antimicrobial peptides of the cathelicidin type. The Dermapur® product is a solution comprising 1.9% of extracts of meadowsweet, *Spiraea ulmaria*. This extract of plants, which is particularly rich in phenolic acids, can in particular inhibit 92% of the growth of *Propionibacterium acnes*, and inhibit 82% of that of *Staphylococcus aureus*, one of the most common Gram-positive bacteria which in particular lead to skin infections in humans.

The Dermapur® product is known to be a bioregulator of skin microflora with an anti-fatty skin and pore treatment activity. Application FR2897778 moreover describes compositions comprising meadowsweet in order to improve the condition of oily and/or acne skin.

Similarly, it has been shown that phenolic plant compounds have antibacterial activity against Gram-positive bacteria, in particular against *Staphylococcus aureus*.

In this way, by stimulating the natural antibacterial defenses, the extract of meadowsweet contributes to cutaneous homeostasis.

Although it is not possible to generalize the work done in humans with the work on animals, the Applicant decided to evaluate the potential of meadowsweet and of boldo on the expression of antimicrobial peptides (such as canine cathelicidin cCath and canine beta-defensin cBD103) on the surface of the skin of animals and their possible interest in treating disorders of the skin of animals (such as canine atopic dermatitis).

The solution to the problem posed has for object a topical composition for animals, characterized in that it comprises, in a physiologically acceptable medium, extracts of boldo *Peumus boldus* and extracts of meadowsweet *Spiraea ulmaria*.

The invention therefore relates in particular to a veterinary composition, i.e. intended for animal care, this care may be therapeutic or non-therapeutic.

Surprisingly, as is shown in particular in the example 1 hereinbelow, the Applicant has been able to demonstrate that the combination of extracts of boldo *Peumus boldus* and extracts of meadowsweet *Spiraea ulmaria* is particularly effective in the developing of a strategy aimed at reducing the appearance and the progression of microbial infections, and as such prevent, treat or also assist with the control of the development of these microbial infections.

Moreover, these plant extracts, taken alone or as a mixture thereof, do not cause the increase of the chimiokine IL-8 or of the cytokine TNF-α. In other words, neither of the two extracts, alone or in combination lead to a pro-inflammatory response.

Inflammation is common in almost all diseases involving lesions of microbial, chemical and physical origin of living tissue. The favorable outcome of this process is the isolation and destruction of the harmful agent, then the repair of the inflammatory lesion so that normal tissue is completely restored. A cute inflammation can be defined as the response of the microcirculation after injury; the cardinal symptoms are heat, redness, pain, swelling and loss of function. Circulatory modifications include vasodilation and migration of white blood cells and leukocytes to the lesion. When, however, the action of the agent persists, inflammation can become chronic and the circulatory modifications characteristic of acute inflammation in this case are replaced with specific chronic injuries, of which the destruction of tissue and fibrous tissue formation. In both cases, the adverse effects of inflammation are significant, and that is why not exacerbating this inflammatory condition while still preventing or treating a microbial infection is interesting.

The combination of the Betapur™ and Dermapur® products appears to be particular effective. The data stemming from studies carried out shows in particular that the two Betapur™ and Dermapur® products, associated in a combination product make it possible to stimulate the expression of cathelicidin cCath synergistically. Indeed, in an atopic dog, it has been observed that the Dermapur® product (known in humans for stimulating cellular synthesis of cathelicidins) at a concentration of 0.2% by weight of the total weight of the product, decreased the expression of cCath cathelicidin in atopic dogs. On the other hand, surprisingly, it has been observed that the Betapur™ product at a concentration of 0.2% by weight of the total weight of the product increased the expression of the cCath cathelicidin.

Even more surprisingly, it has been observed that the composition associating a combination of Betapur™ at a concentration of 0.1% by weight of the total weight of the product (concentration therefore twice as less than the concentration of the Betapur™ product tested alone) with Dermapur® at a concentration of 0.1% by weight of the total weight of the product (concentration also twice as less than the concentration of the Dermapur® product tested alone) made it possible to obtain an effect on the stimulation of cCath cathelicidin that is greater than the sum of the expected effects when these products are taken individually. As such, the association of the Betapur™ and Dermapur® products, and therefore the association of the extracts of boldo *Peumus boldus* and extracts of meadowsweet *Spiraea ulmaria*, make it possible to create an effect that each one of them cannot obtain by acting individually.

The invention also has for object a composition for its use in the preventing, the treating or assisting with the control of microbial infections in animals.

The invention also has for object a composition for its use as a stimulator of the production of antimicrobial peptides.

The invention also has for object the non-therapeutic use of such a composition as a skin disinfectant.

It has as another object the non-therapeutic use of such a composition as an ear cleaner.

It has for additional object a non-therapeutic method for stimulating in an animal cells producing antimicrobial peptides such as cathelicidins and/or beta-defensins, characterized in that a composition according to the invention is applied to the animal.

This invention further relates to a method that makes it possible to reduce microbial proliferation by a topical application of the composition according to the invention, said topical application meaning a local application on the skin or on a mucosa.

Finally, the invention has for final object a method for manufacturing a composition according to the invention, characterized in that within the same formulation are combined a composition containing extracts of boldo *Peumus Boldus* and a composition containing extracts of meadowsweet *Spiraea ulmaria*.

BRIEF DESCRIPTION OF THE DRAWINGS

The invention shall be understood better when reading the following non-limiting description, written in reference to the annexed drawings, wherein.

DETAILED DESCRIPTION OF PARTICULAR EMBODIMENTS

The composition according to the invention comprises, in a physiologically acceptable medium, extracts of boldo *Peumus boldus* and extracts of meadowsweet *Spiraea ulmaria*.

The term physiologically acceptable medium means according to this invention, without limitation, an aqueous or hydro-alcohol solution, a water-in-oil emulsion, an oil-in-water emulsion, a microemulsion, an aqueous gel, an anhydrous gel, a serum, a vesicle dispersion, a powder. Physiologically acceptable means that the compositions are particularly suitable for topical or transdermal use, in contact with mucous membranes, appendages (nails, hair), hair and skin of mammals and more particularly dogs and cats, compositions that can be ingested or injected into the skin, without risk of toxicity, incompatibility, instability, allergic response, and others.

This physiologically acceptable medium forms what is conventionally called the excipient of the composition.

For use according to the invention, the effective quantity of the extracts of boldo *Peumus boldus* and/or of the extracts of meadowsweet *Spiraea ulmaria*, i.e. their dosage depends on various factors, such as age, the skin condition of the animal, etc. An effective quantity means a nontoxic quantity that is sufficient to produce the desired effect.

Boldo, *Peumus boldus* is a shrub from the arid zones of Chile. It has also been acclimatized in the south of France and the Mediterranean countries. The leaf surface, rough, is covered with small vesicles, filled with essential oils. Boldo is a tree species of the Monimiaceae family.

The leaves of boldo contain an alkaloid: boldine. They are known to have particular diuretic, hepatotonic and sedative properties.

Meadowsweet, *Filipendula ulmaria* (also called *Spiraea ulmaria*) is a perennial herb of the Rosaceae family, native to Europe. The leaves and flowers are known to have in particular diuretic, antipyretic, antispasmodic and antirhumatic properties.

According to the invention, the concentration in extracts of boldo of the composition is between 0.00005% to 50%, preferentially between 0.00005% and 10%, preferentially between 0.00005% to 1%, preferentially between 0.0005% and 0.1% and further more preferentially between 0.005% and 0.01% of the total weight of the composition.

The concentration in extracts of meadowsweet of the composition is between 0.00001% and 50%, preferentially between 0.00001% and 10%, preferentially between 0.00001% and 0.2%, preferentially between 0.0001% and 0.02% and further more preferentially between 0.001 and 0.01% by weight of the total weight of the composition.

Those skilled in the art are able to adjust the quantity of extracts according to the effect desired.

More preferably, the concentration in extracts of boldo advantageously contains between 0.005% and 0.01% by weight of the total weight of the composition, and the concentration in extract of meadowsweet advantageously contains between 0.001% and 0.01% by weight of the total weight of the composition.

However, the precise amount of each plant extract (or product comprising a plant extract) is determined by the end use of the composition according to the invention. This choice depends in particular of one or more parameters such as the type of component in which these extracts will be added, the galenic form of the finished product, the species, age, body weight, general health, sex, the type of disease or condition to be treated, the animal to which is intended the composition according to the invention. Consequently, the quantities of ingredients or additional components may vary considerably.

Advantageously, the extracts of boldo *Peumus boldus* contained in the composition according to the invention are derived from a composition, marketed under the name Betapur®, comprising:
  between 10% and 25% by weight of the total weight of the composition of butylene glycol;

between 5% and 10% by weight of the total weight of the composition of extracts of boldo;

between 5% and 10% by weight of the total weight of the composition of pentylene glycol;

between 0.1% and 1% by weight of the total weight of the composition of xanthan gum; and more than 50% by weight of the total weight of the composition of water;

and the extracts of meadowsweet *Spiraea ulmaria* contained in the composition according to the invention are derived from a composition sold under the name Dermapur®, comprising:

between 30% and 70% by weight of the total weight of the composition of butylene glycol;

between 1% and 5% by weight of the total weight of the composition of extracts of meadowsweet *Spiraea ulmaria*;

more than 25% by weight of the total weight of the composition of water.

The Betapur™ product, marketed by the company BASF, comprises the extract of boldo, *Peumus boldus*. The composition of this Betapur™ product is detailed in table 1 hereinbelow:

TABLE 1

Composition of the Betapur ™ product:

| Ingredients | Nom INCI | Percentage |
| --- | --- | --- |
| Demineralized water | Water | >50.00% |
| Butylene glycol | Butylene glycol | 10-25% |
| Boldo | *Peumus Boldus* Leaf Extract | 5-10% |
| Hydrolite-5 | Pentylene Glycol | 5-10% |
| Xanthan Gum | Xanthan Gum | 0.1-1% |

The Dermapur® product, marketed by the company Silab, comprises the extract of meadowsweet, *Spiraea ulmaria*. The composition of this Dermapur® product is detailed in the table 2 hereinbelow:

TABLE 2

Composition of the Dermapur ® product:

| Ingredients | Percentage | CAS NO. | EINECS NO. |
| --- | --- | --- | --- |
| Butylene glycol | 50.00% | 107-88-0 | 203-529-7 |
| Water | 48.10% | 7732-18-5 | 231-791-2 |
| Extract of *Spiraea Ulmaria* | 1.90% | 84775-57-5 | 283-886-3 |

According to the invention, the composition according to the invention comprises a weight ratio between the extracts of boldo and the extracts of meadowsweet between 99 per 1 and 1 per 99, preferentially between 50 per 1 and 1 per 50, even more preferentially between 10 per 1 and 1 per 10, even more preferentially between 10 per 1 and 2 per 1, in a manner further more preferably between 6 per 1 and 3 per 1.

According to a particular embodiment of the invention, the composition comprises as unique plants extracts stimulating cellular synthesis of antimicrobial peptides:

extracts of boldo, *Peumus boldus*, and extracts of meadowsweet *Spiraea ulmaria*.

As it stems from the studies conducted by the Applicant, a composition comprising at least extracts of boldo *Peumus boldus* and/or extracts of meadowsweet *Spiraea ulmaria* is particularly suitable for use in preventing or treating microbial infections. Likewise, such a composition is suited for use in assisting with the control of microbial infections in animals.

Advantageously, the compositions according to the invention are suited for use in preventing, treating or in assisting with the control of microbial infections, in particular *Staphylococcus pseudintermedius* and/or *Malassezia pachydermatis* infections.

According to the invention, the compositions can be used as stimulators of the production of antimicrobial peptides, in particular cathelicidins and/or beta-defensins.

Surprisingly, the composition according to the invention does not stimulate the production of pro-inflammatory cytokines.

Preferably, the animal to which the composition according to the invention is administered has an alteration of the skin barrier.

Skin lesions can in particular be caused by dermatitis (*Malassezia* dermatitis, atopic dermatitis), pyoderma, chronic ear infections or fungal or bacterial infections.

According to another aspect of the invention, the composition object of the invention is administered daily for a short period of at least 3, 5, 7, 15 or 21 days, or for a longer period of at least 1, 2, 3, 4, 5 or 6 months with administration frequencies varying from 1 to 3 times/week.

The various galenic forms that can contain the extracts of boldo and the extracts of meadowsweet according to the invention have any form namely creams, lotions, ointments, milks, gels, emulsions, dispersions, solutions, suspensions, shampoos, transdermal patches, or powders, sprays, ointments, liniments, sprayable formulations, brushable, soaps. The solutions or suspensions which must be applied locally are advantageously presented as spot-on, i.e. they are applied by deposition in one or two localized points, on the skin of the animal. A composition can also be considered in the form of a foam or in the form of a composition for aerosol also comprising a pressurized propellant. The compositions according to the invention can also be for oral and dental health use, for example a toothpaste. In this case, the compositions can contain usual adjuvants and additives for the oral compositions and in particular surfactants, thickening agents, humectants, polishing agents such as silica, various active ingredients such as fluorides, in particular sodium fluoride, and possibly sweetening agents such as sodium saccharin. Advantageously, the composition according to the invention comprises surfactants such as emulsifiers and humectants, chosen from anionic, cationic, amphoteric or non-ionic derivatives, stabilizers such as antioxidants and coloring agents.

Advantageously, the compositions according to the invention can have the form of gels, lotions, oil-in-water or water-in-oil emulsions, dispersions, milks, creams, ointments, foams, shampoos, micellar solutions or any other galenic form suitable for a topical application. These different forms can be prepared by those skilled in the art by techniques currently in use in the cosmetics and pharmaceutical industry.

The compositions according to the invention are advantageously packaging in bottles, water bottles, tubes, spray, aerosols, ear cleansers, pipette, wipes, bags or in any other packaging suitable for a topical application.

Preferentially, the composition is applied to the animal in the form of a shampoo, a lotion, a cream, an ointment, a gel or a suspension as spot-on.

The term topical application means an application that is intended to act on the location where it is applied: skin, mucosa, appendages. The topical use or topical application according to the invention can advantageously target fatigued skin (having for example lost its flexibility), damaged and/or irritated skin (following aggressions of elements such as cold, the sun) or skin injured by scratches, wounds, infections (bacterial or fungal for example). As such the topical application of the composition according to the invention can be carried out, according to the cases and the condition of the animals concerned, on healthy animals, as maintenance for example for skin disinfection and in particular ear cleaning, or on injured and/or sick animals as treatment and as prevention in particular for *Staphylococcus pseudintermedius* and/or *Malassezia pachydermatis* infections.

Improvements in the appearance and in the general state of the skin and mucous membranes and appendages can be obtained by topical application on a regular basis such as every day. The practitioner will appreciate the cosmetic topical treatment that will include a composition containing extracts of boldo *Peumus boldus* and/or the extracts of meadowsweet *Spiraea ulmaria*, this treatment can be achieved for example by topically applying the composition described in this invention, according to a technique usually used to apply such a composition.

The topical application can be cosmetic and/or dermopharmaceutical and/or pharmaceutical.

Preferably, the composition according to the invention is applied to the skin or fur of an animal, which is preferably a cat or a dog.

Advantageously, the composition according to the invention can also comprise one or several additional ingredients well known to those skilled in the art such as in particular, stabilizers, diluents, fragrances, fillers, salts, cleaning agents which can be surfactant agents and/or surfactants and/or emulsifiers, polymers (including the materials obtained by polymerization of the monomer type or obtained from two types of monomers (copolymers) or from several types of monomers), antimicrobial agents, foaming agents, foam synergists, anti-foaming agents, bulking agents, skin protection agents, conditioning agents, film-forming agents, gelling agents, hair conditioners, emulsion stabilizers, emollients, buffering agents, antistatic agents, keratolytic agents, stabilizing agents, chelating agents, antioxidants, antiseborrhoeic agents, reducing agents, abrasives, absorbents, anticaking agents, anticorrosive agents, anti-dandruff agents, antiperspirants, deodorants agents, astringent agents, plasticizers, propellants, binders, denaturing agents, lipid restoring agents, masking agents, coloring agents, pearlescent agents, opacifiers, soothing agents, moisturizers, the smoothing agents, cooling agents, oxidation agents, solvents, toners, UV absorbers, UV filters, viscosity control agents.

The antioxidants can advantageously be chosen from tocopherol and its esters such as tocopheryl acetate; BHT and BHA.

The antimicrobial agents which may be used in the composition according to the invention are preferably chosen from 2,4,4'trichloro-2'-hydroxy diphenyl ether (or triclosan), 3,4,4'-trichlorobanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopiroxe, ciclopiroxo lamine, undecylenic acid and salts thereof, benzoyl peroxide, 3-hydroxy benzoic acid, 4-hydroxy benzoic acid, phytic acid, N-acetyl L-cysteine acid, lipoic acid, azelaic acid and salts thereof, arachidonic acid, resorcinol, 2,4,4'trichloro-2'-hydroxy diphenyl ether, 3,4,4'-trichlorocarbanalide, octopirox, octoxyglycerine, octanoylglycine, caprylyl glycol, 10-hydroxy-2-decanoic acid, copper pidolate, salicylic acid, zinc salicylate, iodopropynyl butylcarbamate, famesol, phytosphingosines and mixtures thereof.

As surfactant agent may be mentioned anionic, cationic, zwitterionic surfactants (e.g. sulfonate, sulfate, carboxylate, phosphonate, phosphate derivatives) amphoteric and uncharged (i.e. macrogols) and a mixture of the latter.

Stabilizers include substances that tend to increase the shelf life of the composition such as preservatives, emulsifiers, thickeners, packaging gases, gelling agents, hydrotropes, humectants, sequestering agents, synergists or stabilizers.

Among the diluents there may be mentioned insoluble mineral salts or sparingly soluble in water such as alkaline earth metal carbonates of magnesium or of zinc, alkali metal titanates or alkaline earth metal, titanium dioxide, metal oxides such as iron oxides, zinc oxide, tin oxide, alkaline earth metal sulfates such as calcium sulfate or barium sulfate, phosphate mono-, di- or tri-basic such as calcium hydrogen phosphate, tricalcium phosphate or magnesium phosphate.

The composition according to the invention is intended for animals, and preferentially for a domestic animal, i.e. an animal coming from domestication and from breeding. This includes livestock, farmyard animals, aquatic animals or pets. Preferably, the domestic animal is a pet chosen from mammals (canines, felines, equines, lagomorphs, rodents). Advantageously, the composition according to the invention is intended for dogs and cats, however, the term pet also includes exotic pets such as for example the ferret, rodents (for example the hamster), lagomorphs (such as for example, the rabbit), the minipig.

In an aspect of the invention, the composition according to the invention is intended for dogs. The composition and the methods according to the invention are more particularly intended for dogs that have an alteration in the skin barrier. This is the case in particular of atopic dermatitis. It is a disease with a racial predisposition. These dog breeds may be cited, but not limited to: Boston Terrier, Cairn Terrier, Dalmatian, English Bulldog, English Setter, Golden Retriever, Golden Retriever Irish Setter, Shar-pei, Labrador Retriever, Lhasa Apso, Miniature Schnauzer, Pug, Scottish Terrier, West Highland White Terrier, Wirehaired Fox Terrier, Boxer, German Shepherd, Poodle, Fox Terrier, American Cocker Spaniel, Terrier Chow Chow, Pyrenean Shepherd, Belgian Shepherd Dog, Shih Tzu, Chihuahua, Yorkshire Terrier Gordon Setter.

Dogs that are not purebred but have similar characteristics of said races can also be treated using the composition according to this invention.

In an embodiment of the invention, the composition according to the invention can be administered in combination with drugs commonly prescribed to animals suffering from microbial infection or alteration of the skin barrier or any other pharmaceutical agent intended to fight external parasites such as fleas, ticks, lice that may cause alterations of the skin leading for example the animal to scratch. Particular mention will be made of insecticides agents such as fipronil, imidaclopride, amitraz, permethrin, methoprene, pyriproxyfen and any other active ingredient capable of preventing or treating infestations by ectoparasites.

The composition can in particular also include systemic and topical antibiotics, such as aminoglycosides, such as gentamicin, streptomycin, amikacin, neomycin, tobramycin, kanamycin; beta-lactams such as penicillins (amoxicillin with or without clavulanic acid for example), penicillin G, ampicillin, but also cephalosporins with cephalexin, cefovecin, the cefadroxil, cefquinome, cefpodoxime, or ceftiofur. Systemic and topical antibiotics also include cyclins such as tetracyclines, oxytetracyclines, doxycycline, but also macrolides (with erythromycin, the azithromycin, spiramycin), lincosamides such as clindamycin, lincomycin, and also fluoroquinolones: enrofloxacin, marbofloxacin, pradofloxacin, difloxacin, orbifloxacine. Also considered as such sulfamides with sulfamethoxypyridazine, sulfamethoxazole (with or without trimethoprim), sulfadiazine, but also rifamycins such as rifampin, polypeptides with in particular colistin, or other antibiotics such as metronidazole, or fusidic acid.

It can also be administered in combination with systemic and topical antifungals, and in particular polyenes, such as amphotericin B, nystatin and griseofulvin, as well as azoles such as fluconazole, itraconazole, posaconazole, miconazole, enilconazole, ketoconazole, fluconazole, climbazole, or allylamines with in particular terbinafine.

The composition according to the invention may also contain antiseptics, such as for example chlorinated products such as sodium hypochlorite (and Dakin solute), halogenated products with iodine products (which comprises iodine and its derivatives such as alcohol or iodine tincture of iodine), iodophors such as povidone iodine, but also biguanides (such as chlorhexidine), alcohols, quaternary ammonium compounds: benzalkonium chloride, bromide cetrimemium, or oxidants, such as hydrogen peroxide (i.e. oxygenated water). Antiseptics also include carbanilides such as triclocarban, and triclosan, but also other molecules, such as benzoyl peroxide, ethyl lactate, piroctone olamine, benzoic acid, acetic acid, boric acid, hexetedine, EDTA with or without sorting, PCMX.

In the same way, the composition may also include immunomodulators, in particular corticosteroids (prednisolone, prednisone, dexamethasone, betamethasone, hydrocortisone, hydrocortisone aceponate, mometasone, triamcinolone, prednicarbate, clobetasol, fluticasone), calcineurin inhibitors (cyclosporine, tacrolimus), interferons, essential fatty acids, antihistamines. It can also be combined with restructurizers and rehydrating agents with ceramides, fatty acids, cholesterol or urea, but also with sebomodulators such as vitamin B6, or zinc.

This non-exhaustive list of different drugs usually prescribed to animals suffering from microbial infection or alteration of the skin barrier is well known to those skilled in the art.

The composition according to the invention can also comprise substances other than the plant extracts of boldo *Peumus boldus* and of meadowsweet *Spiraea ulmaria* detailed hereinabove, in particular other extracts of plants, raw materials of food (plant, animal, minerals), amino acids, proteins, essential oils, fats (fatty acids in particular), minerals, vitamins or medicated active substances.

As detailed in the trials presented hereinbelow, according to the invention, the composition is advantageously used for the treating, the preventing or the assisting with the control of microbial infections. In the framework of this invention, the term "assisting with the control of microbial infections" means a means of supplying a support to the epidermal barrier and/or to the innate microbial immune defenses during microbial infections in animals.

According to an alternative, the invention consists of a composition comprising in a physiologically acceptable medium extracts of boldo *Peumus boldus* and/or in a composition comprising in a physiologically acceptable medium extracts of meadowsweet *Spiraea ulmaria*. Said compositions can be used combined together or separately for their use in the preventing, treating or the assisting with the control of bacterial infection in animals. These compositions according to the invention can be applied topically on the skin or the fur of an animal, preferentially a cat or a dog. The concentration in extracts of boldo is between 0.00005% to 50%. The concentration in extracts of meadowsweet is between 0.00001% and 50%. This alternative of the invention also has for object, the use of each one of these compositions, in combination or separately, as a stimulator of the production of antimicrobial peptides, such as cathelicidins and/or beta-defensins, without however stimulating the production of pro-inflammatory cytokines.

In an alternative of the invention, the composition can be administered daily and this, throughout the life of the animal. In another alternative, the composition can also be administered on a regular basis 1, 2, 3 times a day or every 2, 3, 4 days, 1, 2, 3 times a week or 1, 2, 3, 4 times a month.

In another alternative, the composition may also be administered in the form of a cure or treatment cycle. That is to say that the administration of the composition, whether daily or not, is made over a defined period of time, between 1 week to one year, more particularly for 1, 2, 3, 4, 5 or 6 months. In an alternative of the invention, the composition according to the invention is administered at least 2, 3, 4, 5, 6 or more times to the animal. In an embodiment, the composition is administered in the form of a cure of 1, 2, 3, 4, 5, 6 or several months, 1, 2, 3 times per year. In a particular alternative of the invention, the composition is administered daily, for a period between 1 and 6 months, in the form of a cure that is renewable once or twice a year.

In another particular alternative, the composition is administered daily for a period of at least 1, 2, 3, 4, 5 or 6 months.

The composition according to the invention is administered in a dose and at a frequency that can be chosen and adjusted by those skilled in the art.

In an aspect of the invention, the composition is used for non-therapeutic purposes, for example to improve the general condition of the animal. Indeed, the composition according to the invention can have an energizing effect, an effect on the reduction of cellular aging and consequently reduce the incidence of diseases and promote the recovery of the animal after sickness or an accident, or also increase vitality. These benefits will be visible in an improvement in the aesthetic appearance of the animal (shiny coat, better posture), its tone, by improving his behavior (interaction with his master, sleep, appetite, pleasure in playing), improving the general condition will also prevent the installation of opportunistic diseases.

Example 1: Evaluation of the Effect In Vitro of Plant Extracts on the Production of Antimicrobial Peptides and Markers of Inflammation in Canine Keratinocytes As indicated hereinabove, antimicrobial peptides (AMPs) are small peptides produced by epithelial and immune cells. They play an important role in innate microbial immune defense. Beta-defensins (BDs) and cathelicidins (Cath) are the most studied AMPs.

The objective of this study is twofold. It is to:
test whether the plant extracts are able to stimulate the production of canine BD103 and/or canine Cath on canine keratinocytes in primary culture;
evaluate their pro-inflammatory response (production of cytokines) in the cell culture supernatant.

This study was conducted in two phases. Phase I was carried out on 10 dogs of the Beagle race, 5 normal and 5 atopic. Phase II was carried out on 14 atopic dogs of the Beagle race.

This study was performed on 10 dogs of the Beagle race, 5 regular and 5 atopic. Three 8 mm biopsies were performed on each dog. The keratinocytes were collected using standard sampling and culture techniques. They were distributed into 24 plates of 48 culture wells as such.

Culture medium suitable for the culture of primary keratinocytes (Cn-T09™ medium, marketed by the company Cellntech) of dog was used. Cholera toxin was added to this medium. The medium was changed every 3 days until 70% confluence. The cells were then cultured in a medium depleted of cell growth factors for 24 hours and then various concentrations of extracts of boldo and meadowsweet were added for 24 hours.

The boldo extract was tested at different concentrations (2%, 1.5%, 1%, 0.4% and 0.2%). The extract of boldo corresponds to the Betapur™ product marketed by the company BASF which comprises the extract of boldo, *Peumus boldus*. The composition of this Betapur™ product is detailed in table 1 hereinabove.

The extract of meadowsweet is tested at different concentrations (1%, 0.4% and 0.2%). The extract B corresponds to the Dermapur® product marketed by the company Silab which comprises the extract of meadowsweet, *Spiraea ulmaria*. The composition of this Dermapur® product is detailed in table 2 hereinabove.

All concentrations were tested in duplicate. After collecting the supernatant, the cells were lysed and mRNA was extracted for molecular analysis. The Kolmogorov-Smirnov normality test was used (alpha=0.05). The means values and the confidence intervals of 95% were calculated for all outcomes. The differences between each extract and its control were compared using the paired t test. The values of p≤0.05 were considered as significant.

Figure 1:
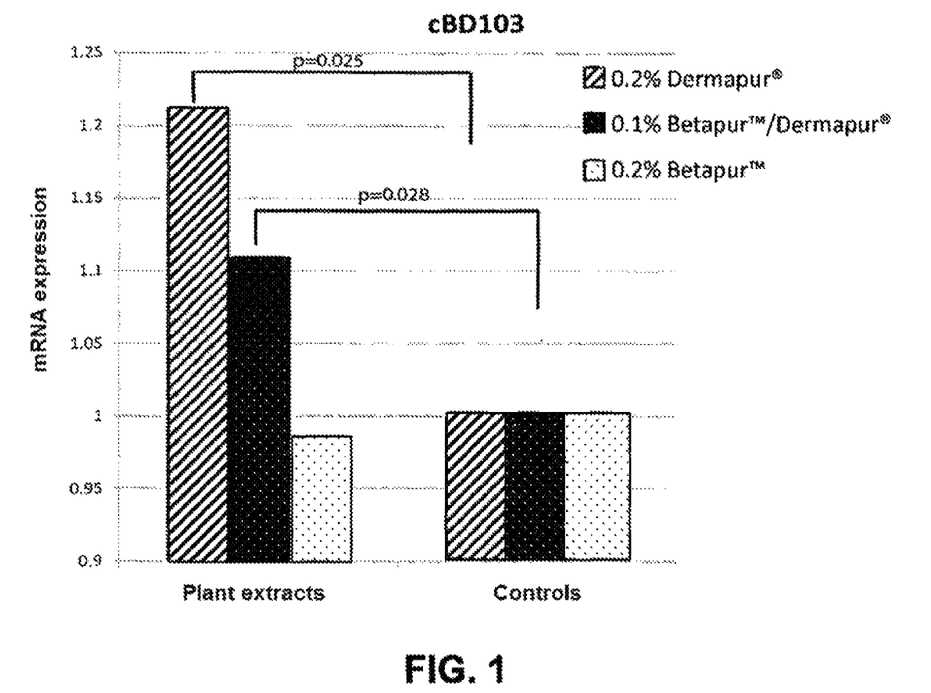
FIG. 1 shows the results of studies of the effects of the Betapur™ and/or Dermapur® products on the levels of mRNA expression of the beta-defensin cBD103. More particularly, the products tested are:
  Betapur™ at a concentration of 0.2% (which means that the extract of boldo *Peumus Boldus* is between 0.01% and 0.02% by weight of the total weight of the product);
  Dermapur® at a concentration of 0.2% (which is equal to 0.0038% by weight of the total weight of the product as extract of meadowsweet *Spiraea ulmaria*), and
  a Betapur™ 0.1%/Dermapur® 0.1% mixture (which means that the extract of boldo *Peumus Boldus* is between 0.005% and 0.01% by weight of the total weight of the product, and that the extract of meadowsweet *Spiraea ulmaria* is equivalent to 0.0019% by weight of the total weight of the product)
Figure 2:
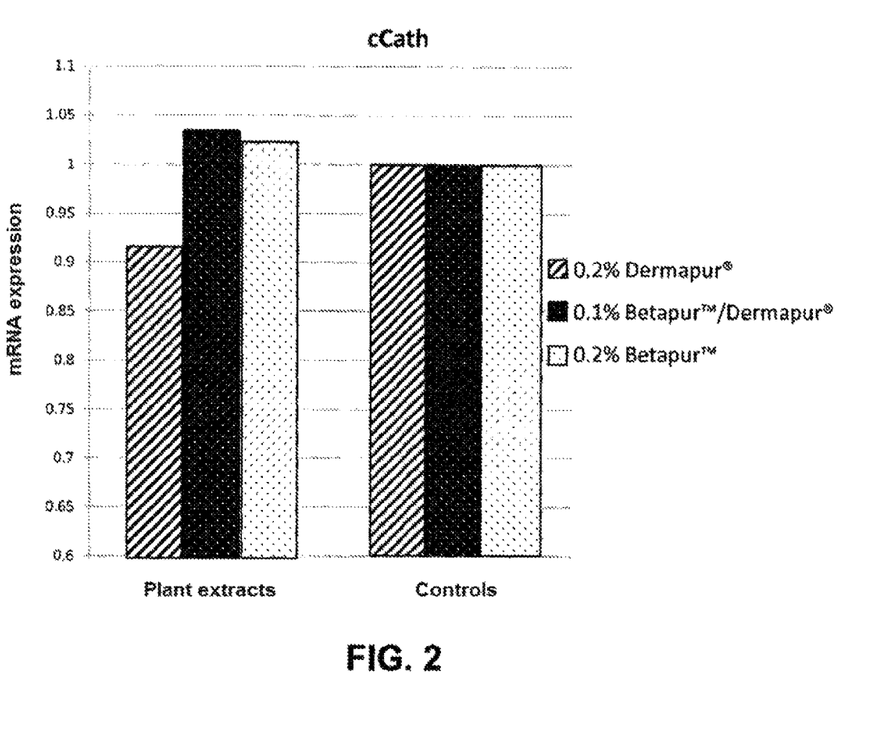
FIG. 2 shows the results of studies of the effects of the same Betapur™ and/or Dermapur® products, at the same concentrations as in FIG. 1 on the levels of mRNA expression of the cCath cathelicidin.

Results concerning phase I:
The studies made it possible to reveal that:
(i) in keratinocytes from normal dogs (healthy), none of the Betapur™ or Dermapur® products, alone or in combination, significantly increases the expression of beta-defensin cBD103 and of cCath cathelicidin.
(ii) in keratinocytes from normal dogs (healthy), none of the Betapur™ or Dermapur® products has a significant effect on the production of TNF-α, cytokine involved in inflammation and in particular on the skin.
(iii) in keratinocytes from normal dogs (healthy), the Betapur™ product does not have any significant effect on the production of Interleukin-8 (IL-8), chemokine that in particular recruits neutrophils. On the other hand, the Dermapur® product, at a concentration of 1% increases the production of Interleukin-8 (IL-8).
(iv) As is shown in FIG. 1, in keratinocytes from atopic dogs, it has been observed that both:
the Dermapur® product at a concentration of 0.2%, and
the composition comprising a combination 0.1% of Dermapur® combined with 0.1% Betapur™;
significantly increased the expression of beta-defensin cBD103 (p=0.025 and p 0.028, respectively). On the other hand, particular surprisingly, the Betapur™ product at a concentration of 0.2%, known in humans to stimulate the expression of human beta-defensin hBD-3 does not increase the expression of beta-defensin cBD103 in atopic dogs.
(v) As is shown in FIG. 2, in the keratinocytes obtained from atopic dogs, it has been observed particularly surprisingly that the Dermapur® product, known in humans to stimulate cell synthesis of the cathelicidins, decreased the expression of cathelicidin cCath (p=0.0615) in atopic dogs. On the other hand, it was observed that both the Betapur® product and the composition comprising a combination of 0.1% of Dermapur® combined with 0.1% Betapur™ increase the expression of the cathelicidin cCath.

Figure 3:
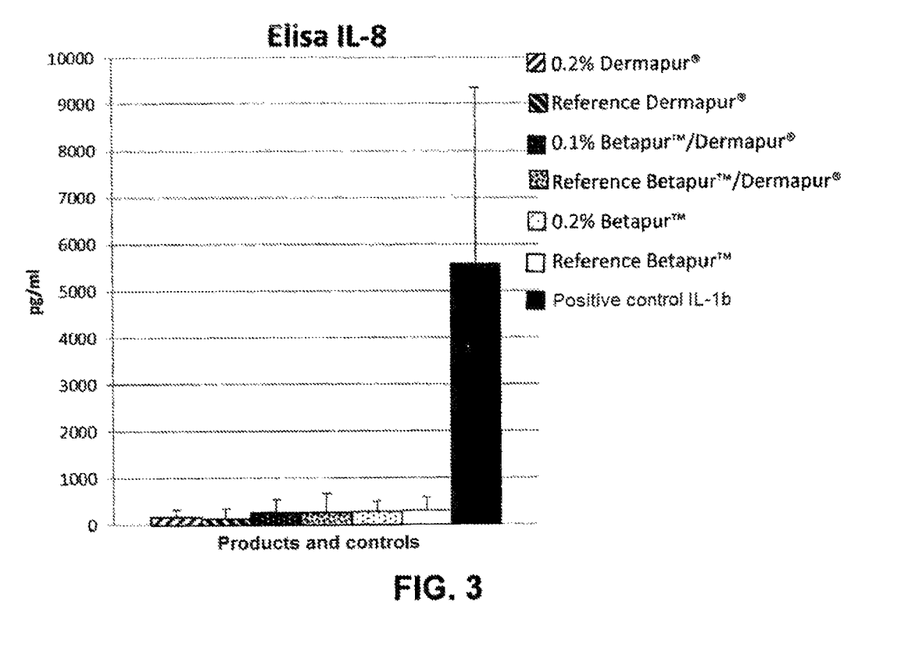
FIG. 3 shows the results of studies of the effects of the same Betapur™ and/or Dermapur® products, on the secretion of interleukin IL-8.
Figure 4:
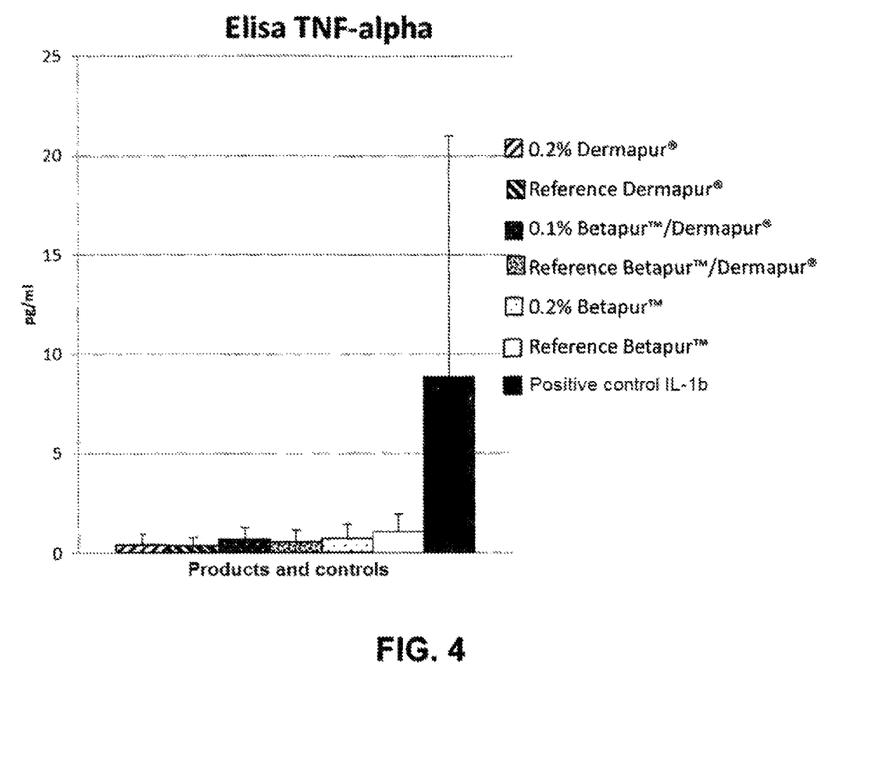
FIG. 4 shows the results of studies of the effects of the same Betapur™ and/or Dermapur® products, on the secretion of TNF-alpha.

Results Concerning Phase II:
(vi) Finally, as is shown in FIGS. 3 and 4, none of the Dermapur® 0.2%, Betapur™ 0.2% products or the combination comprising 0.1% Dermapur® combined with 0.1% Betapur™ causes the increase of the chemokine IL-8 or of the cytokine TNF-α. In other words, neither of the two products or the composition comprising a combination of the two products causes a pro-inflammatory response.

Example 2: Shampoo According to the Invention

In an example that is particularly suited for the controlling of infections via *Malassezia pachydermatis*, the composition according to the invention is a shampoo comprising in a physiologically acceptable medium extracts of boldo *Peumus boldus* and extracts of meadowsweet *Spiraea ulmaria*.

For use of this shampoo, the Applicant has determined the quantity of product to be administered, which varies depending on the weight of the animal being considered. This quantity must be adapted to both the size of the animal and the length of the hair coat. It can be applied according to the criteria described in the following table:

| Weight of the animal | Volume of product |
| --- | --- |
| 4.9 kg | 10 ml × 2 baths |
| 5.0 to 10.9 kg | 15 ml × 2 baths |
| 11.0 to 15.9 kg | 20 ml × 2 baths |
| 16.0 to 20.9 kg | 25 ml × 2 baths |
| 21.0 to 30.9 kg | 30 ml × 2 baths |
| 31.0 to 45.9 kg | 40 ml × 2 baths |
| 46.0 kg | 50 ml × 2 baths |

The invention claimed is:
1. Topical composition for animals, comprising, in a physiologically acceptable medium, an extract of boldo *Peumus boldus* and an extract of meadowsweet *Spiraea ulmaria*,
wherein the extract of boldo represent from 0.00005% to 1% by weight of a total weight of the composition, and wherein the extract of meadowsweet represent from 0.00001% to 0.2% by weight of the total weight of the composition,
wherein the composition is formulated as a skin disinfectant for an animal or as an ear cleaner for an animal.
2. The composition according to claim 1, which is formulated to be applied on the skin or the fur of an animal.
3. The composition according to claim 2, wherein the animal is a cat or a dog.
4. The composition according to claim 2, which is formulated to be applied to the animal in the form of a shampoo, a lotion, a cream, an ointment, a gel or a solution or a suspension as spot-on.
5. The composition according to claim 1, wherein the extract of boldo represent from 0.005% to 0.01% by weight of the total weight of the composition, and wherein the extract of meadowsweet represent from 0.001% to 0.01% by weight of the total weight of the composition.

6. The composition according to claim 1, wherein a weight ratio between the extract of boldo and the extract of meadowsweet is in a range from 99:1 to 1:99.

7. The composition according to claim 1, which is formulated for use in preventing, treating or in assisting with the control of microbial infections in the animal.

8. The composition according to claim 7, which is formulated for use in preventing, treating or in assisting with the control of *Staphylococcus pseudintermedius* and/or *Malassezia pachydermatis* infections.

9. The composition according to claim 1, which is formulated for use as a stimulator of the production of antimicrobial peptides.

10. The composition according to claim 9, wherein the antimicrobial peptides are cathelicidins and/or beta-defensins.

11. The composition according to claim 1, which does not stimulate the production of pro-inflammatory cytokines.

12. The composition according to claim 2, wherein the animal has an alteration of the skin barrier.

13. The composition according to claim 12, wherein the animal is afflicted with skin lesions caused by an affection selected from the group consisting of *Malassezia* dermatitis, atopic dermatitis, pyoderma, chronic ear infections, fungal infections, and bacterial infections.

14. The composition according to claim 3, which is in the form of a shampoo, a lotion, a cream, an ointment, a gel or a solution or a suspension as spot-on.

15. The composition according to claim 1, wherein a weight ratio between the extract of boldo and the extract of meadowsweet is in a range from 10:1 to 1:10.

16. The composition according to claim 1, wherein the animal is a pet selected from the group consisting of canines, felines, equines, lagomorphs, rodents and ferrets.

17. Method of disinfecting skin, comprising applying a composition according to claim 1 as a skin disinfectant, wherein the composition is formulated as a skin disinfectant.

18. Method of cleaning an ear, comprising applying the composition according to claim 1 as an ear cleaner, wherein the composition is formulated as an ear cleaner.

19. Method of stimulating in an animal cells producing antimicrobial peptides, comprising applying the composition according to claim 1 to the animal.

20. Method for manufacturing a topical composition, comprising combining within the same formulation:
 a composition containing an extract of boldo *Peumus Boldus*, and
 a composition containing an extract of meadowsweet *Spiraea ulmaria*,
 so as to obtain the composition according to claim 1.

21. Method of stimulating in an animal cells producing antimicrobial peptides including at least one of cathelicidins and beta-defensins, comprising applying the composition according to claim 1 to the animal.

* * * * *